United States Patent
Zhu et al.

(10) Patent No.: US 10,591,335 B2
(45) Date of Patent: Mar. 17, 2020

(54) CORIOLIS MASS FLOW MEASURING DEVICE AND/OR DENSITY MEASURING DEVICE

(71) Applicant: Endress + Hauser Flowtec AG, Reinach (CH)

(72) Inventors: Hao Zhu, Freising (DE); Alfred Rieder, Landshut (DE); Ennio Bitto, Aesch (CH)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 0 days.

(21) Appl. No.: 15/537,904

(22) PCT Filed: Nov. 18, 2015

(86) PCT No.: PCT/EP2015/076919
§ 371 (c)(1),
(2) Date: Jun. 20, 2017

(87) PCT Pub. No.: WO2016/102122
PCT Pub. Date: Jun. 30, 2016

(65) Prior Publication Data
US 2017/0350742 A1 Dec. 7, 2017

(30) Foreign Application Priority Data

Dec. 22, 2014 (DE) .................. 10 2014 119 427
May 18, 2015 (DE) .................. 10 2015 107 769

(51) Int. Cl.
*G01F 1/84* (2006.01)
*G01N 9/00* (2006.01)

(52) U.S. Cl.
CPC .......... *G01F 1/8477* (2013.01); *G01F 1/8413* (2013.01); *G01N 9/002* (2013.01)

(58) Field of Classification Search
CPC ........................................................ G01F 1/84
See application file for complete search history.

(56) References Cited

U.S. PATENT DOCUMENTS

| 4,781,069 A | 11/1988 | Mitzner |
| 5,370,002 A | 12/1994 | Normen |

(Continued)

FOREIGN PATENT DOCUMENTS

| CN | 11 27550 A | 7/1996 |
| CN | 10 3562690 A | 2/2014 |

(Continued)

OTHER PUBLICATIONS

European Search Report in corresponding European Patent Application No. 15795194.8, dated Sep. 18, 2018.

(Continued)

*Primary Examiner* — Jewel V Dowtin
(74) *Attorney, Agent, or Firm* — Bacon & Thomas, PLLC

(57) ABSTRACT

A Coriolis mass flow measuring device and/or density measuring device includes two bent measuring tubes, which extend mirror symmetrically to a first mirror plane between the measuring tubes, an actuator arrangement and at least one sensor arrangement. At the inlet end and at the outlet end, a collector, with which the measuring tubes are joined, wherein the collectors each fulfill the functionality of a node plate. A support body, which connects the collectors rigidly with one another; and inlet end and outlet end, in each case, at least one plate-shaped coupler, which connect the measuring tubes pairwise with one another, in order to form an oscillator. The couplers have tube openings for measuring tubes, wherein the measuring tubes are connected at least sectionally with the couplers, wherein inlet end and outlet end, in each case, at least one coupler has, between the (Continued)

measuring tubes, a tuning opening for influencing the oscillation characteristics of the oscillator.

35 Claims, 7 Drawing Sheets

(56) References Cited

U.S. PATENT DOCUMENTS

| | | | | |
|---|---|---|---|---|
| 6,308,580 B1* | 10/2001 | Crisfield | ............... | G01F 1/8409 |
| | | | | 73/861.355 |
| 6,415,668 B1* | 7/2002 | Cage | .................... | G01F 1/8413 |
| | | | | 73/861.355 |
| 6,666,098 B2* | 12/2003 | Drahm | .................. | G01F 1/8413 |
| | | | | 73/861.355 |
| 7,325,461 B2* | 2/2008 | Bitto | .................... | G01F 1/8409 |
| | | | | 73/861.355 |
| 7,325,462 B2* | 2/2008 | Bitto | .................... | G01F 1/8409 |
| | | | | 73/861.355 |
| 7,802,484 B2* | 9/2010 | Pankratz | ................... | G01F 1/74 |
| | | | | 73/861.355 |
| 7,845,241 B2* | 12/2010 | Van Cleve | ............ | G01F 1/8409 |
| | | | | 73/861.355 |
| 8,573,067 B2* | 11/2013 | Lanham | ................ | G01F 1/8418 |
| | | | | 73/861.355 |
| 8,613,228 B2 | 12/2013 | Hussain | | |
| 9,109,936 B2* | 8/2015 | Drahm | .................. | G01F 1/8431 |
| 2005/0098688 A1 | 5/2005 | Miarka | | |
| 2012/0255369 A1 | 10/2012 | Rieder | | |

FOREIGN PATENT DOCUMENTS

| | | |
|---|---|---|
| CN | 10 4204735 A | 12/2014 |
| DE | 102011010178 A1 | 8/2012 |
| DE | 102011006971 A1 | 10/2012 |
| DE | 102014119427 A1 | 6/2016 |
| DE | 102015107769 A1 | 11/2016 |
| EP | 1529997 A2 | 5/2005 |
| EP | 2 559 976 A1 | 2/2013 |
| WO | 2007/057385 A1 | 5/2007 |
| WO | 2009014871 A1 | 1/2009 |
| WO | 2012/136671 A1 | 10/2012 |
| WO | 2013149817 A1 | 10/2013 |
| WO | 2014172115 A1 | 10/2014 |

OTHER PUBLICATIONS

German Search Report, German Patent Office, Munich, DE, dated Aug. 6, 2015.
International Search Report, EPO, The Netherlands, dated Feb. 12, 2016.
Office Action dated Mar. 27, 2019, issued in corresponding Chinese Application No. 201580070587.6.

* cited by examiner

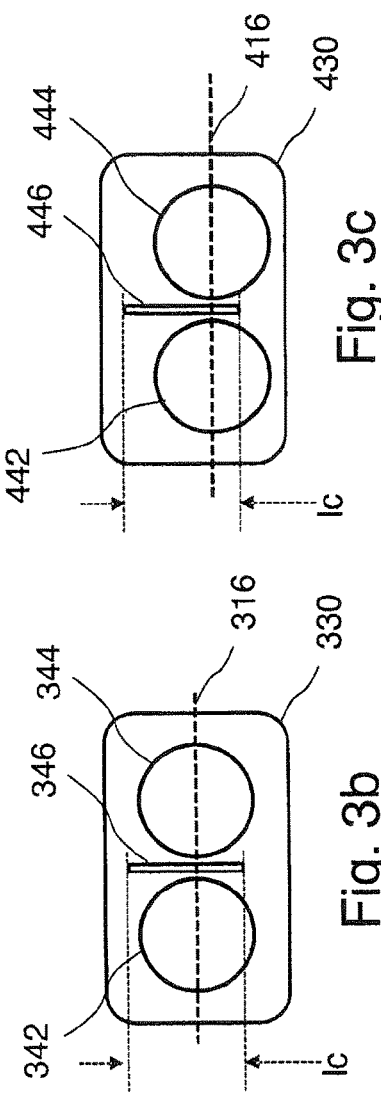
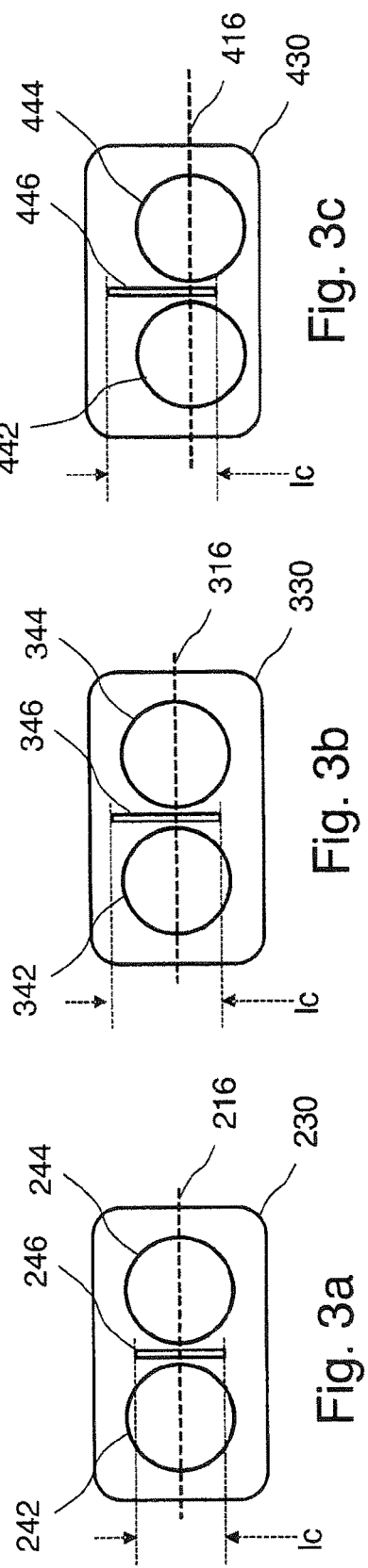
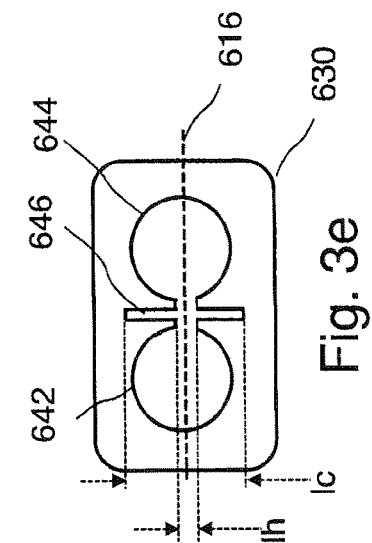
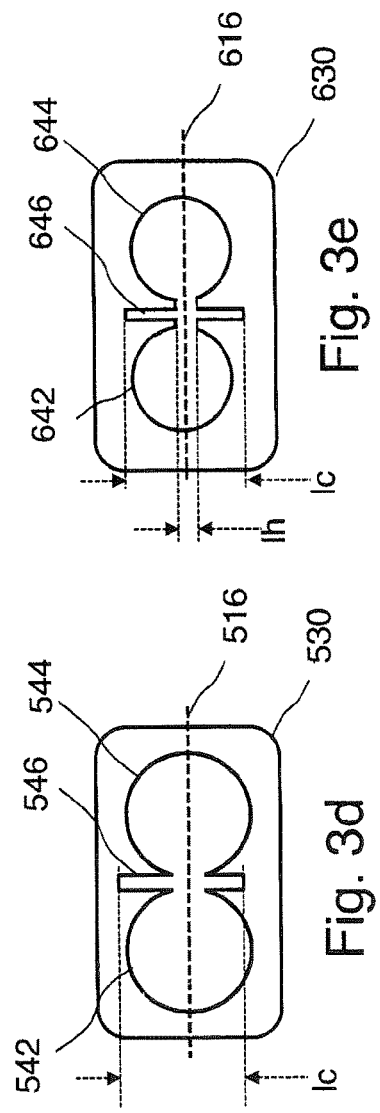
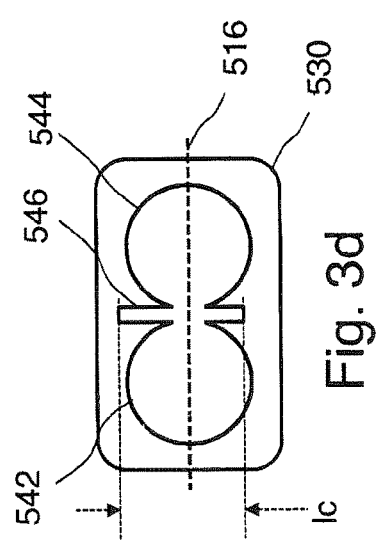

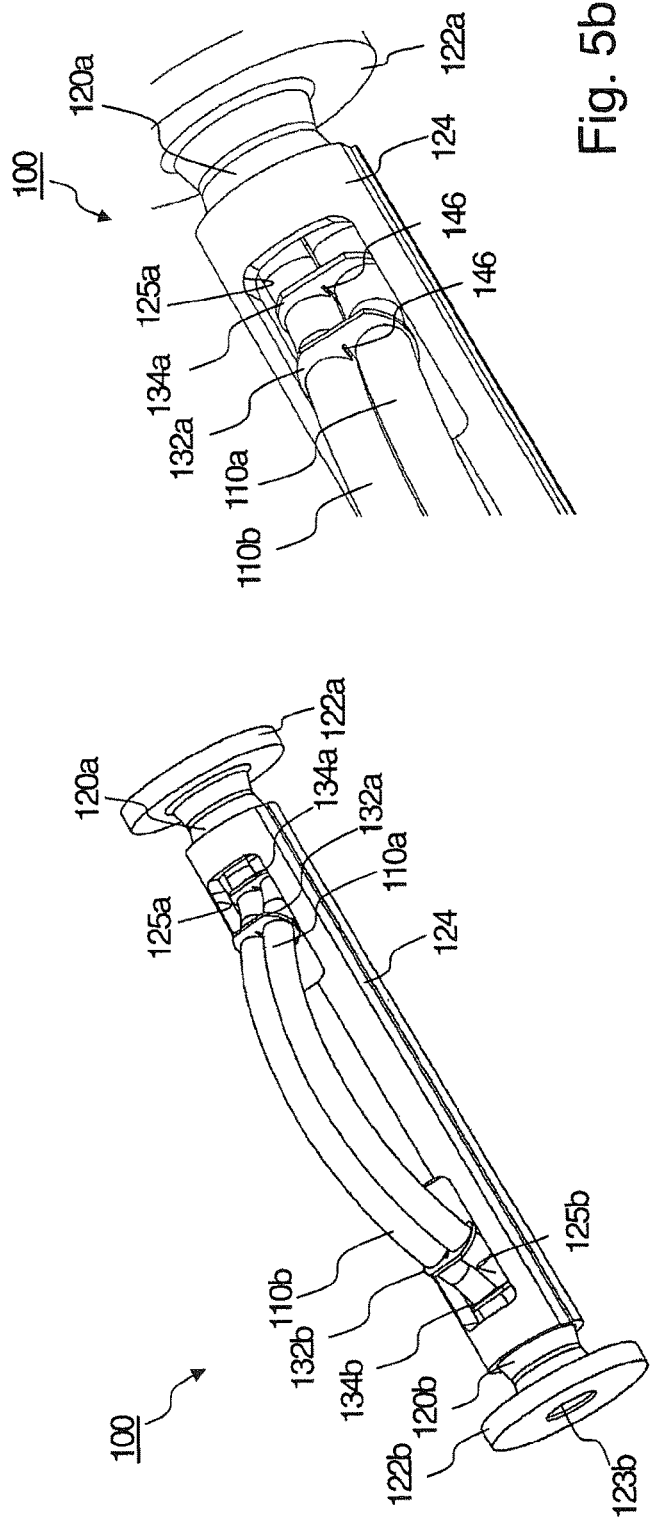
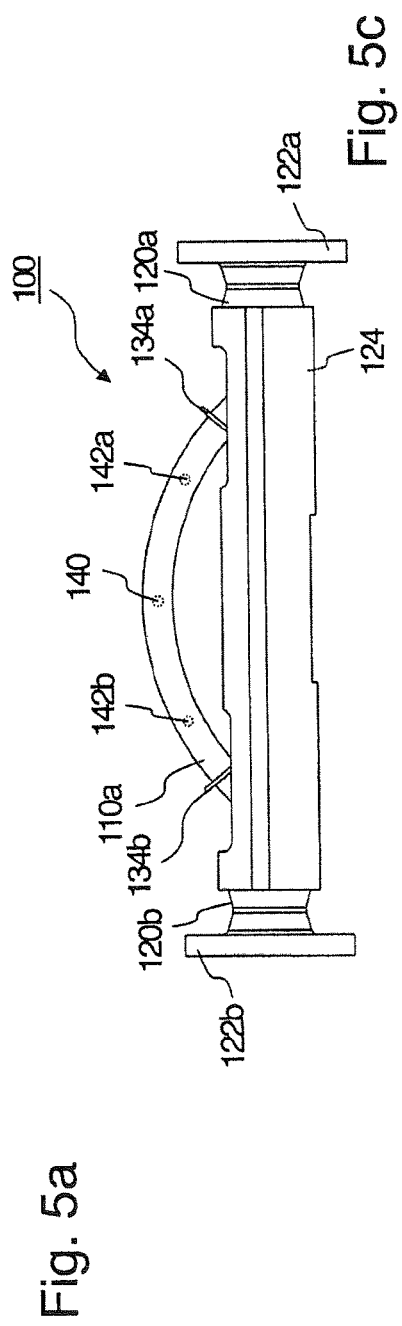

CORIOLIS MASS FLOW MEASURING DEVICE AND/OR DENSITY MEASURING DEVICE

TECHNICAL FIELD

The present invention relates to a Coriolis mass flow measuring device and/or density measuring device (in the following CMD) comprising: at least two bent measuring tubes, at least one actuator arrangement and at least one sensor arrangement; collectors, one at inlet ends of the measuring tubes and one at outlet ends of the measuring tubes, wherein the measuring tubes are joined inlet end and outlet end with collectors. The inlet end and outlet end collectors are embodied stably in such a manner that each fulfills the function of a node plate; a support body, which connects the inlet end collector and the outlet end collector rigidly with one another; and inlet end and outlet end, in each case, at least one, especially two or more, couplers. The measuring tubes are connected pairwise with one another by means of the couplers, in order to form an oscillator, and the couplers are arranged spaced from one another and from the collectors in the direction of the measuring tube axes. The couplers have, in each case, two tube openings for the measuring tubes connected by the couplers, through which openings the measuring tubes are led, wherein the measuring tubes are connected along their peripheries at least sectionally with the couplers, wherein the actuator arrangement is adapted to excite a bending oscillation wanted mode between the two measuring tubes of the oscillator and the sensor arrangement is adapted to register oscillations of the oscillator.

The resonant frequency of the bending oscillation wanted mode is a measure for the density of a medium flowing through the measuring tubes. The phase difference between the two sensor signals of the sensor arrangement depends on the mass flow.

BACKGROUND DISCUSSION

CMD of the field of the invention are disclosed, for example, in German patent publications, DE 10 2011 006 971 A1, and DE 10 2011 006 919A1; and US 2013/0319134 A1, and U.S. Pat. No. 8,281,668 B2 and U.S. Pat. No. 6,415,668 B1 as well as in U.S. Pat. No. 5,370,002 and US 2015/0033874 A1. In general, the couplers serve, by their coupling of the measuring tubes, to form an oscillator with defined oscillation characteristics.

Investigations of CMD of the field of the invention in connection with the present invention have shown that the vibrations of their oscillators still dissipate oscillatory energy to the environment, especially to a connected fluid line. Conversely, in the same way, disturbing oscillations can be in-coupled into the oscillator. Both effects can degrade the performance of a CMD significantly.

SUMMARY OF THE INVENTION

It is, therefore, an object of the present invention to provide a CMD, in the case of which the above disturbance effects are ameliorated, or prevented.

The CMD of the invention includes: at least two bent measuring tubes, wherein the measuring tubes have measuring tube axes, which extend mirror symmetrically to a first mirror plane, which extends between the measuring tubes; at least one actuator arrangement; and at least one sensor arrangement; inlet end and outlet end, in each case, a collector, wherein the measuring tubes are joined inlet end and outlet end with collectors, wherein the inlet end and outlet end collectors are embodied stably in such a manner that each fulfills the functionality of a node plate; a support body, which connects the inlet end collector and the outlet end collector rigidly with one another; and inlet end and outlet end, in each case, at least one, preferably two or more, plate-shaped couplers, wherein the measuring tubes are connected pairwise with one another by means of the couplers, in order to form an oscillator, wherein the couplers have, in each case, two tube openings for the measuring tubes connected by the couplers, through which openings the measuring tubes are led, wherein the measuring tubes are connected along their peripheries at least sectionally with the couplers, wherein the actuator arrangement is adapted to excite a bending oscillation wanted mode between the two measuring tubes of the oscillator, and the sensor arrangement is adapted to register oscillations of the oscillator, wherein inlet end and outlet end, in each case, at least one coupler has, between the measuring tubes connected by the couplers a tuning opening surrounded by a closed edge for influencing the oscillation characteristics of the oscillator. The closed edge extends, in such case, especially in the plane of the plate-shaped coupler.

The couplers are arranged inlet- and outlet end spaced from the collectors.

To the extent that inlet- and outlet end a plurality of couplers are present, these are arranged spaced from one another in the direction of the measuring tube axes.

By means of suitable positioning of the plate-shaped coupler, cross sensitivity to vibrations from the environment, or the dissipating of oscillatory energy to the environment, especially to a connected fluid line, can be reduced to a certain degree. Since, however, different interaction mechanisms are present, which comprise, on the one hand, forces, and, on the other hand, moments, or torques, which act on the inlet- and outlet end collectors, the two cannot be optimally minimized via only one control parameter, such as the position of the coupler. Thus, here, the tuning openings offer additional degrees of freedom, with which the disturbing, interacting mechanisms can be largely eliminated.

In a further development of the invention, the tuning openings have in the first mirror plane an extension of at least 30%, for example, at least 50%, and especially at least 75% of the diameter of the measuring tubes.

In a further development of the invention, the tuning openings have in the first mirror plane a length, whose square amounts to not less than twice, for example, not less than four times and especially not less than eight times the area of the tuning opening.

In a further development of the invention, the separation of the measuring tube axes at the position of the tuning opening amounts to no more than 1.5 times the outer diameter of the measuring tubes, especially no more than 1.3 times the outer diameter and preferably no more than 1.2 times the outer diameter.

In a further development of the invention, at least one coupler includes in its coupler plane a convex envelope, whose area amounts to no more than five times, especially no more than 4½ times, especially no more than four times the outer area of a measuring tube cross section.

In a further development of the invention, at the inlet end and at the outlet end, in each case, at least two couplers of a measuring tube pair connected by the couplers have such a tuning opening.

In a further development of the invention, at the inlet end and at the outlet end, in each case, at least the two inner couplers of a measuring tube pair connected by the couplers have such a tuning opening, wherein the two inner couplers are the couplers farthest from the respective collector.

In a further development of the invention, the at least one tuning opening is essentially symmetric to the first mirror plane.

In a further development of the invention, at the inlet end and at the outlet end, in each case, the tuning opening of at least one coupler is asymmetric with reference to a second coupler specific coupler normal plane, wherein the coupler normal plane extends parallel to the greatest principal axis of inertia of the coupler, perpendicular to the first mirror plane, and contacts a connecting line of the measuring tube axes extending perpendicular to the first mirror plane within the tuning opening.

In a further development of the invention, the separation of the outermost extension of the at least one tuning opening in the first mirror plane from the coupler normal plane on a first side of the coupler normal plane is less than on a second side of the coupler normal plane.

In a further development of the invention, the separation between the outermost extension of the tuning opening in the first mirror plane and the outermost extension of the coupler in the first mirror plane on a first side of the coupler normal plane is less than on a second side of the coupler normal plane.

In a further development of the invention, at the inlet end and at the outlet end, in each case, at least one coupler has a center of mass, which is removed from the coupler normal plane by a separation, wherein the separation amounts to, for example, not less than 4%, especially not less than 8%, of the separation of the measuring tube axes in the coupler normal plane.

In a further development of the invention, at the inlet end and at the outlet end, in each case, at least one coupler has a center of area of a minimum convex envelope, which center of area is removed from a coupler normal plane by a separation, wherein the separation amounts to, for example, not less than 4%, especially not less than 8%, of the separation of the measuring tube axes in the coupler normal plane.

In a further development of the invention, at the inlet end and at the outlet end, in each case, a first coupler and a second coupler have coupler specific coupler normal planes, which, in each case, extend parallel to the greatest principal axis of inertia of the respective couplers, which extend perpendicular to the first mirror plane, and which contact a connecting line of the measuring tube axes extending perpendicular to the first mirror plane within the tuning openings of the respective couplers, wherein the first coupler has a first center of mass, which is spaced from its coupler specific coupler normal plane by a first separation, wherein the second coupler has a first center of mass, which is spaced from its coupler specific coupler normal plane by a second separation, wherein the first separation differs from the second separation, wherein the difference amounts, for example, to not less than 5%, especially not less than 10%, of the smaller of the two separations.

In a further development of the invention, at the inlet end and at the outlet end, in each case, a first coupler and a second coupler have coupler specific coupler normal planes, each of which extends parallel to the greatest principal axis of inertia of its coupler, each of which extends perpendicular to the first mirror plane, and each of which contacts a connecting line of the measuring tube axes extending perpendicular to the first mirror plane within the tuning opening of its coupler, wherein at the inlet end and at the outlet end, in each case, a first coupler has a first center of area of a minimum convex envelope curve and a second coupler has a second center of area of a minimum convex envelope curve, wherein the first center of area is spaced from its coupler specific coupler normal plane by a first separation, wherein the second center of area is spaced from its coupler specific coupler normal plane by a second separation, wherein the first separation differs from the second separation, wherein the difference amounts, for example, to not less than 5%, especially not less than 10%, of the smaller of the two separations.

In a further development of the invention, at the inlet end and at the outlet end, in each case, a first coupler and a second coupler have coupler specific coupler normal planes, each of which extends parallel to the greatest principal axis of inertia of its coupler, each of which extends perpendicular to the first mirror plane, and each of which contacts a connecting line of the measuring tube axes extending perpendicular to the first mirror plane within the tuning opening of its coupler, wherein the first coupler has a first tuning opening, wherein the second coupler has a second tuning opening, and wherein the first tuning opening differs from the second tuning opening in at least one of the following parameters: area of the tuning opening, length of the tuning opening, separation of the center of area of the tuning opening from its coupler normal plane.

The above described symmetry differences of the plate-shaped couplers and the tuning openings represent other degrees of freedom, which can be used for optimizing the oscillator characteristics, wherein, such as indicated above, the minimizing of the cross sensitivities to vibrations from the environment are a prime concern. These symmetry differences can be additionally be used to minimize mechanical stresses, which occur on the oscillator, especially on the measuring tubes and the couplers, which, in turn, contributes to the long term stability of the structure and therewith to the reproducibility of the measured values.

In a further development of the invention, at the inlet end and at the outlet end, in each case, at least one tuning opening is bounded by edge sections, which in a section between the measuring tubes are formed on both sides by the measuring tubes.

In a further development of the invention, the edge sections formed by the measuring tubes have perpendicular to the greatest principal axis of inertia of the respective coupler, in each case, a length, which amounts to not less than 10%, especially not less than 20%, and preferably not less than 30%, of the radius of the measuring tube, which forms the particular edge section of the tuning opening.

Actually in the case of conventional couplers, stress maxima occur in the region between the measuring tubes, when the measuring tubes are joined there with couplers. When the measuring tubes now according to the further development of the invention form an edge section of the tuning opening, this means that they have in this edge section a free lateral surface, whereby the mechanical stress peaks are significantly lessened in this region.

The coupler of the CMD of the invention enables suppression of out-coupling of an oscillatory energy from the CMD and suppression of in-coupling of disturbing oscillations from a pipeline, in which the CMD is installed. This suppression is especially effective when, at the inlet end and at the outlet end, in each case, two couplers with tuning openings are provided. Especially when the couplers are embodied to be sufficiently stiff, the transferring of such oscillatory components from the measuring tubes to the collectors is suppressed, which, due to symmetry effects, contribute only slightly to the out-coupling of oscillatory energy, which symmetry effects, however, nevertheless bring about oscillating stresses on the connections between the measuring tubes and the collectors. Such oscillating stresses can lead, over time, to damaging of the connections, and to a concomitant risk of leakage. Insofar, the CMD of the invention has due to the minimizing of these oscillating stresses also a reduced risk of downtime because of leakage. In the case of a given material thickness and a given tuning opening length, a sufficiently high stiffness of the couplers can be achieved by a small tuning opening area.

In a further development of the invention, the plate-shaped couplers have a material thickness, which amounts to no more than four times, especially no more than three times, the wall thickness of the measuring tubes.

The measuring tubes, according to a further development of the invention, comprise a metallic material, especially stainless steel. The couplers and or the collectors comprise, in each case, a material compatible as regards coefficient of thermal expansion, especially the same metallic material.

The CMD of the invention can comprise a pair, two pairs or more pairs of coupled measuring tubes, wherein especially each pair of coupled measuring tubes of the CMD is embodied according to the above description for a measuring tube pair.

In a further development of the invention, the CMD includes, at the inlet end and at the outlet end, in each case, a collector, which joins the measuring tubes of two measuring tube pairs of the CMD.

In a further development of the invention, the first mirror plane of the first measuring tube pair is at the same time the first mirror plane of a second measuring tube pair of the CMD of the invention.

BRIEF DESCRIPTION OF THE DRAWINGS

The invention will now be explained based on examples of embodiments illustrated in the drawing, the figures of which show as follows:

FIG. 3a: is a first example of an embodiment of a coupler of a CMD of the invention;

FIG. 3b: is a second example of an embodiment of a coupler of a CMD of the invention;

FIG. 3c is a third example of an embodiment of a coupler of a CMD of the invention;

FIG. 3d is a fourth example of an embodiment of a coupler of a CMD of the invention;

FIG. 3e is a fifth example of an embodiment of a coupler of a CMD of the invention;

FIG. 5a: is a simplified perspective total view of an example of an embodiment of a CMD of the invention;

FIG. 5b: is a detail of the view of FIG. 5a; and

FIG. 5c: is a simplified side view of the example of an embodiment of a CMD of the invention of FIGS. 5a and 5b.

DETAILED DISCUSSION IN CONJUNCTION WITH THE DRAWINGS

First, some of the geometric terms used in the following will be explained based on FIGS. 1a, 1b, 1c and 1d.

Figure 1B:
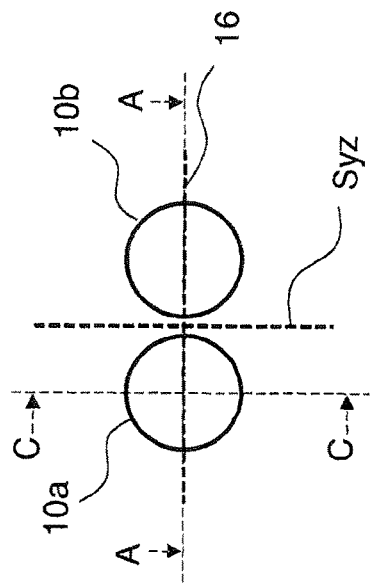
FIGS. 1a to 1c: are sketches of a CMD for explanation of some geometrical terms for description of the invention.
Figure 1D:
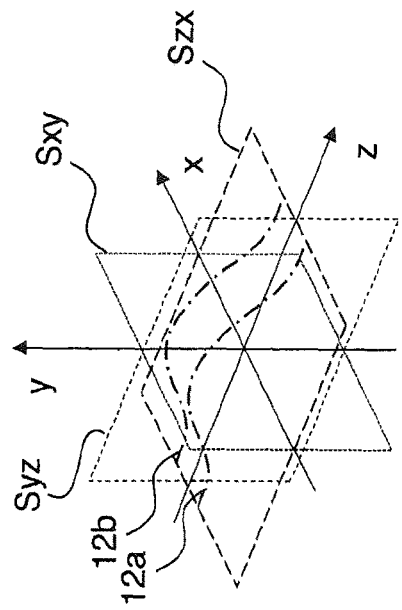
FIG. 1d: is a coordinate system for description of the invention.
Figure 1A:
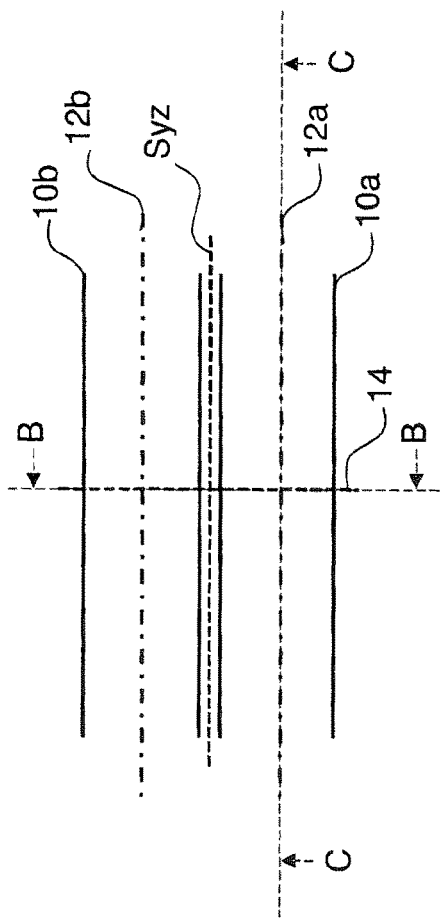
Figure 1C:
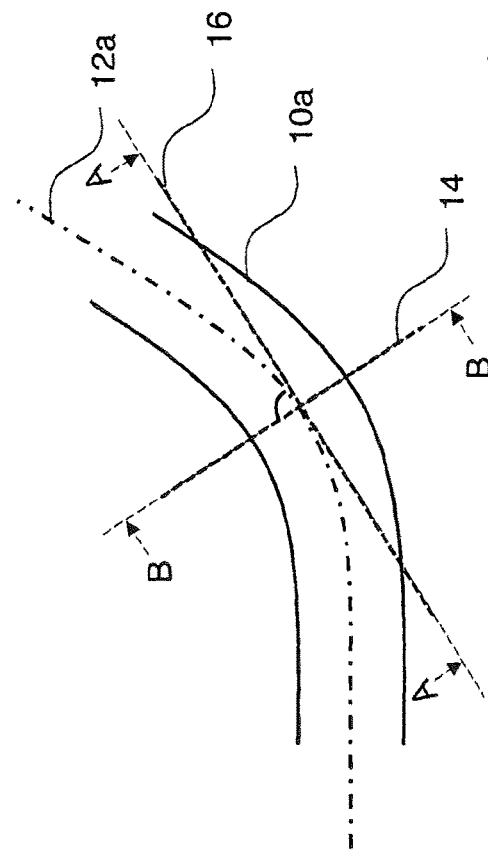

FIG. 1a shows a plan view of a section of two parallel measuring tubes 10a, 10b of a CMD. A corresponding sectional view taken on the cutting plane B-B of FIG. 1a is shown in FIG. 1b, while FIG. 1c shows a longitudinal section through one of the measuring tubes 10a taken on the cutting plane C-C of FIG. 1. The measuring tubes 10a, 10b have measuring tube axes 12a, 12b, which are defined along the courses of the measuring tubes, in each case, by the midpoints of the tube cross-sections of minimum cross sectional area. The measuring tube axes extend symmetrically to a first mirror plane Syz, which extends between the measuring tube axes 12a, 12b.

Each measuring tube axis 10a, 10b extends symmetrically to a second mirror plane Sxy, which extends perpendicular to the first mirror plane Syz. The line of intersection between the first mirror plane Syz and the second mirror plane defines the Y-axis of a coordinate system for description of the CMD. A third plane Szx extends perpendicular to the first and second mirror planes. In the case of a two tube CMD with bent measuring tubes, this plane is not a mirror plane. Insofar, the positioning of the third plane is arbitrary, but it does fix the zero-point of the Y-axis. The CMD of the invention have at the inlet end and at the outlet end, in each case, a collector, which, usually, has a process connection flange with an essentially axially symmetric connection surface, whose axis of symmetry coincides with the Z-axis. The third plane Szx intersects the first mirror plane Syz along the Z-axis. Correspondingly, the third plane Szx intersects the second mirror plane Sxy along the X-axis.

The measuring tubes 10a, 10b are, according to the invention, connected pairwise by plate shaped couplers, which are not shown in FIGS. 1a to 1c. The maximum principal axis of inertia of each coupler, thus that axis with the largest moment of inertia, extends perpendicular to a coupler plane 14, in which the center of mass of the coupler lies. The coupler plane 14 can be a plane normal to the measuring tube axes; this is, however, not absolutely required. The maximum principal axis of inertia extends parallel to the first mirror plane Syz and lies especially in the first mirror plane.

Perpendicular to the first mirror plane Syz and perpendicular to the coupler plane 14 extends a coupler specific coupler normal plane 16, in which the coupler plane 14 and a connecting line of the measuring tube axes 12a, 12b coincide.

The exciting of the measuring tubes occurs, usually, in the X-direction, and, indeed, especially with an actuator, which is arranged in the second mirror plane Sxy.

The problem to which the invention is directed will now be explained briefly based on FIG. 2a, which shows an inlet end, or outlet end, of a CMD 100 in side view. The measuring tubes 110 stands in communication with a collector 120, which is connected with a flange 122, whose end face serves for connecting the CMD 100 to a pipeline. The measuring tubes 110 are connected pairwise by means of an inner coupler 132 and an outer coupler 134. The collector 120 is connected via a rigid support body 124 with a second collector (not shown) at the other end of the CMD 100, in order to suppress movements of the collectors relative to one another.

Figure 2A:
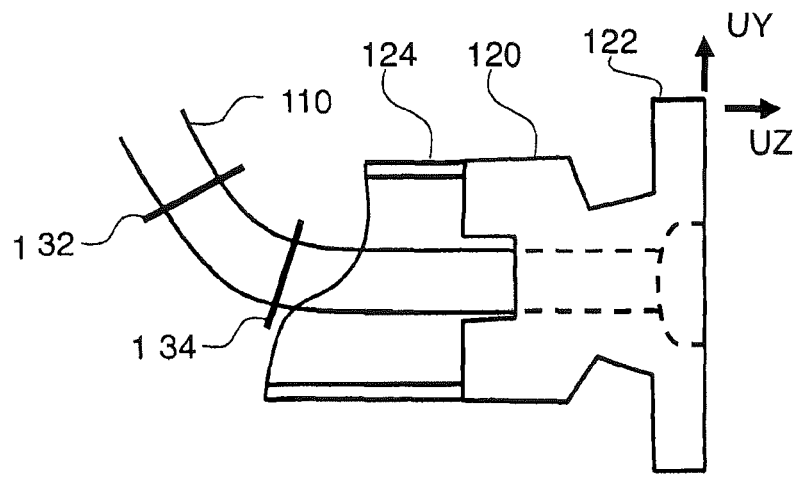
FIG. 2a: is a schematic representation of a detail of a CMD for purposes of explaining a goal of the present invention.

As indicated by the arrows UY and UZ, the oscillations of the measuring tubes, which are excited in the X-direction, thus in the representation of FIG. 2a perpendicular to the plane of the drawing, bring about a coupled movement of the collector 120, respectively the flanges 122 connected therewith. These movements can degrade the performance of the measuring device and are, consequently, to be minimized.

An objective function OBJ to be minimized for evaluation of success is, for example:

$$OBJ = \frac{1}{U_s} \sqrt{\frac{\int |\vec{U}|^2 dA}{A}}$$

In such case, the magnitude squared of a locationally dependent movement vector (UY,UZ) is integrated over the area of the face of the flange 122, and the integral is normalized with the area of the face. By taking the square root of this value divided by the amplitude of a sensor movement Us in the X-direction, the objective function OBJ is defined, which is to be minimized. The sensor movement Us is the movement of an oscillation sensor 142a, 142b, whose position along the measuring tubes is shown in FIG. 5c.

The position p1 of the inner coupler 132 along the measuring tubes is only limitedly available as a degree of freedom for minimizing the objective function OBJ, since the position p1 establishes the free oscillatory length of the measuring tubes and therewith essentially co-determines the eigenfrequency of the oscillator comprising the measuring tubes as well as the sensitivity dφ/d□ of the CMD 100, wherein the angle φ describes a phase difference between the positions of the oscillation sensors 142a, 142b of the oscillator illustrated in FIG. 5c.

Figure 2B:
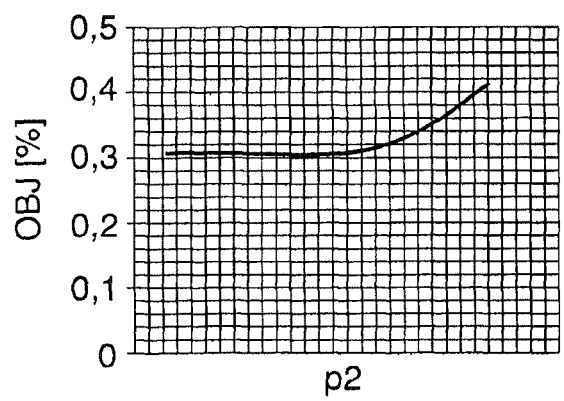
FIG. 2b: is a graph for explaining the influence of a coupler position on an objective function of the CMD design.

The position of the outer coupler 134 is therewith, first of all, the remaining degree of freedom, with which the objective function OBJ can be influenced. As shown in FIG. 2b, the position p2 of the second coupler 132 along the measuring tube does actually have an influence on the objective function, and a minimum of OBJ(p2) can be found, which amounts, for example, to about 0.3025%. This value is, indeed, not bad, it can, however, still be improved.

Figure 2C:
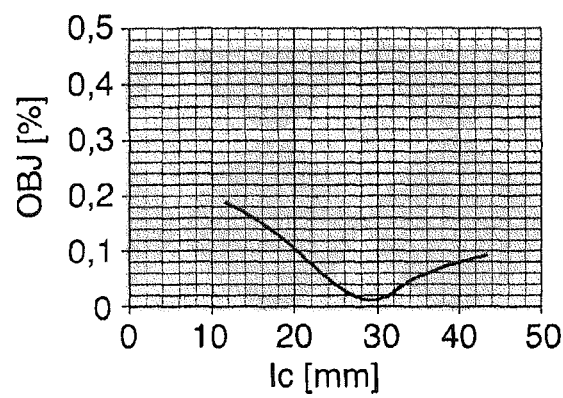
FIG. 2c: is a graph for explaining the influence of the tuning opening length on an objective function of the CMD design.

FIG. 2c shows now the influence of tuning openings of length Ic in the couplers 132, 134 on the objective function OBJ(Ic), wherein the optimal position of the second coupler ascertained according to FIG. 2b is maintained. The two couplers are equally embodied and have, in each case, symmetry of the point group $D_{2h}$. It is found that the objective function OBJ(Ic) has at, for instance, 30 mm a minimum, which here amounts, for instance, to 0.0122%.

The concrete dimensions of the couplers and the tuning openings as well as the values for the objective function OBJ achievable therewith are, of course, dependent on other parameters of the CMD, such as measuring tube diameter, measuring tube length, arc height of the measuring tubes and number of couplers, I to be determined, for example, by simulation by means of FEM.

FIGS. 3a-d show views of examples of embodiments of couplers 230, 330, 430, 530, 530 of a CMD of the invention. The couplers comprise, in each case, a planar metal plate and have two tube openings 242, 244; 342, 344; 442, 444; 542, 544 for the measuring tubes to be coupled, which extend through the metal plate, wherein a tuning opening of length Ic extends between the tube openings. The material thickness of the metal plate amounts, for example, to about three tube wall thicknesses of the measuring tubes to be coupled. The measuring tubes are secured in the tube openings, for example, by means of a hard solder.

The illustrated couplers 230; 330; 430; 530; 630 differ as regards other features, which will be explained in the following, for example, by symmetry deviations relative to the coupler normal plane 216; 316; 416; 516; 616, which, according to the above definition, extends parallel to the greatest principal axis of inertia of the couplers and in which the coupler plane and a connecting line of the measuring tube axes coincide, wherein the measuring tube axes extend in the coupler plane through the midpoints of the tube openings 242, 244; 342, 344; 442, 444; 542, 544; 642, 644.

The first example of an embodiment of a CMD coupler 230 shown in FIG. 3a has a symmetry of the point group $D_{2h}$. Here, accordingly, the center of area of the tuning opening 246 and the center of area of the coupler plate lie in the coupler normal plane 216.

The second example of an embodiment of a coupler 330 of a CMD of the invention shown in FIG. 3b includes, in contrast with FIG. 3a, a tuning opening 346, whose center of area lies outside of the coupler normal plane 316.

In the case of the third example of an embodiment of a coupler 430 of a CMD of the invention shown in FIG. 3c, in contrast with FIG. 3a, both the center of area of the tuning opening 446 as well as also the center of area of the coupler are arranged outside of the coupler normal plane 416.

The fourth example of an embodiment of a coupler 530 of a CMD of the invention shown in FIG. 3d includes, in contrast with FIG. 3a, a tuning opening 546, whose center of area lies outside of the coupler normal plane 516. Furthermore, the circumferences of the tube openings 542, 544 intersect an overlap region of the tuning opening 546, so that the tuning opening 546 is connected with the tube openings. The length of the overlap region perpendicular to the coupler normal plane amounts, for example, to not less than 10%, especially not less than 20% and preferably not less than 30% of the radius of the tube openings 542, 544. In the mounted state of the couplers in a CMD, measuring tubes extend through the tube openings, which then in the overlap region form an edge section of the tuning opening. In the overlap region, the measuring tubes remain free of solder.

In the case of the fifth example of an embodiment of a coupler 630 of a CMD of the invention shown in FIG. 3e-such as in the case of the fourth example of an embodiment—the tuning opening 646 is connected with the tube openings. In contrast with FIG. 3d, here, the tuning opening 646 includes in a central region a broadening, which extends to the tube openings 642, 644, so that the tuning opening 546 is connected with the tube openings. The length Ih of the broadening perpendicular to the coupler normal plane amounts, for example, to not less than 10%, especially not less than 20% and preferably not less than 30% of the radius of the tube openings 642, 644.

In the mounted state of the couplers in a CMD, measuring tubes extend through the tube openings to then form an edge section of the tuning opening. In this section, the measuring tubes remain free of solder.

The design degree of freedom illustrated based on FIGS. 3a-e, such as the presence, or the amount, of a deviation from the symmetry illustrated in FIG. 3a, or the presence, or the amount, of an overlap region between the tuning opening and the circumference of the tube openings, can be combined as much as desired. Furthermore, the tube openings can also have cross sections deviating from the circular shape, for example, elliptical.

The deviations from the symmetry in the design of a coupler and/or design differences between different couplers enable further minimizing of the stresses arising on the couplers, which contributes to the long term stability of the measuring characteristics of the CMD.

The mutually facing outer surface segments of the measuring tubes have, especially near the coupler normal plane, stress maxima in the oscillatory state. A joint in this region, for example, a solder connection is, consequently, likewise exposed to large stresses, a factor that contributes to its fatigue. Couplers, which have tube openings open to the tuning opening, prevent this problem, since then the outer surface segments, which are exposed to the large stresses, can move freely.

Figure 4A:
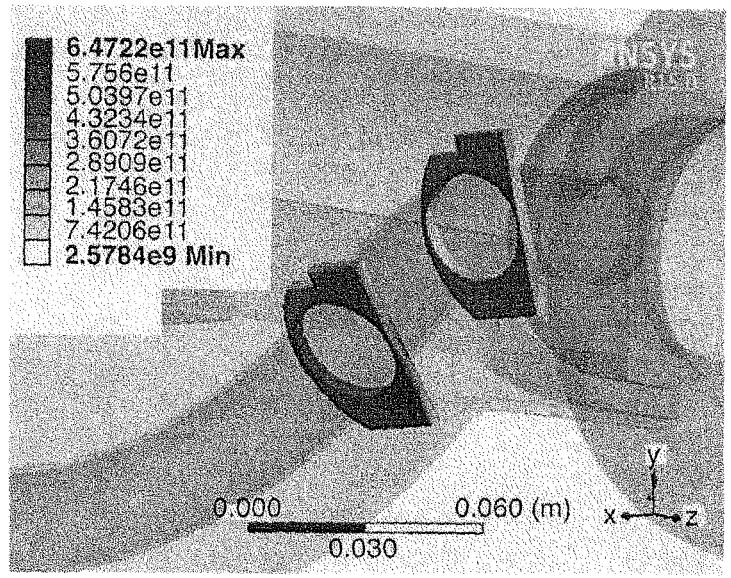
FIG. 4a: are simulation results for mechanical stress distributions in the couplers of a CMD of the state of the art.
Figure 4B:
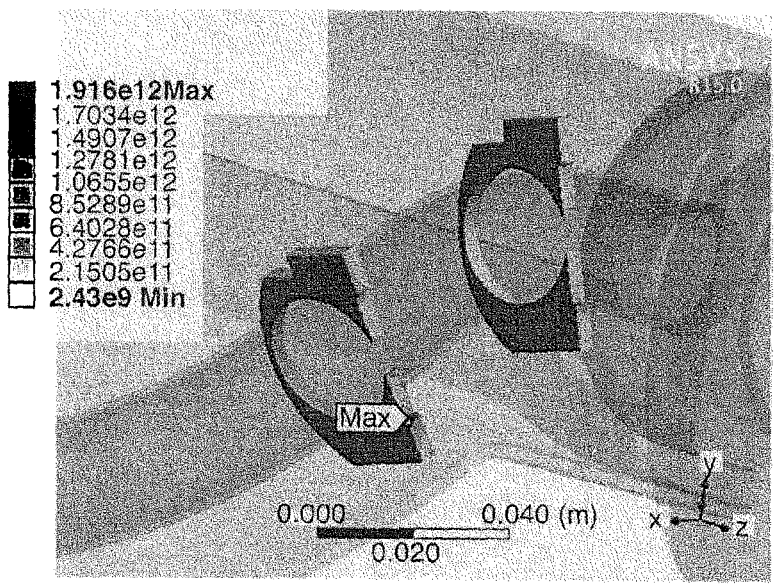
FIG. 4b: are simulation results for mechanical stress distributions in the couplers of a first example of an embodiment of a CMD of the invention.
Figure 4C:
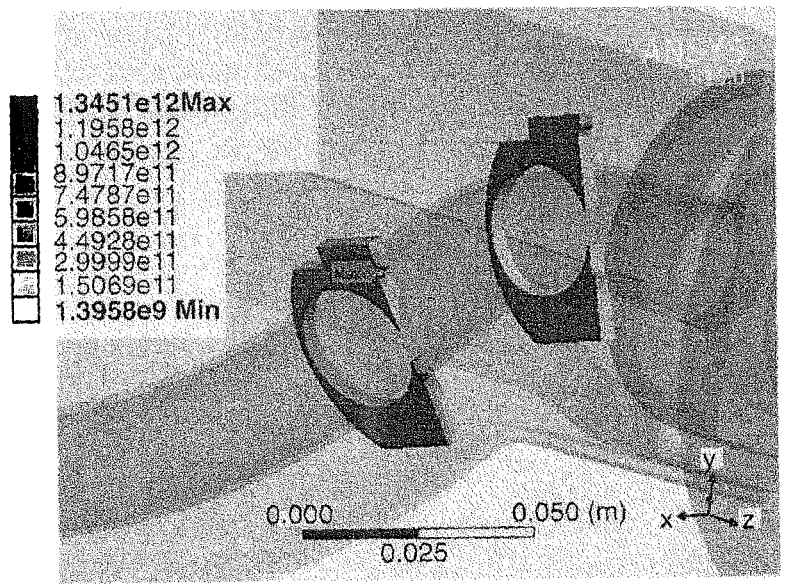
FIG. 4c: are simulation results for mechanical stress distributions in the couplers of a second example of an embodiment of a CMD of the invention.

FIGS. 4a, 4b and 4c show simulation results for the mechanical stress distributions in the couplers of a CMD having two inlet end and two inlet end couplers. The numerical values are, however, not to be considered as absolutes, since they were calculated with extremely exaggerated oscillation amplitudes. In the present case, of importance is only a comparison of the relative values.

In the case of the couplers of a CMD of the state of the art according to FIG. 4a, the stress maximum occurs on the inner coupler near the coupler normal plane and amounts in the case of a given oscillation amplitude of the measuring tubes, for example, to about $6.5 \times 10^{11}$.

The CMD of the invention according to FIG. 4b includes couplers with tuning openings, whose centers of area lie in the coupler normal plane. Insofar as here the coupling forces must be absorbed by the rim of the tuning opening of the coupler, it is not surprizing that locally greater stresses occur than in the case of the solid coupler of FIG. 4a. Actually, a maximum value is present, which with, for instance, $1.9 \times 10^{12}$ amounts to just about three times the maximum value of the solid coupler. The stress maximum lies on the narrow lateral edge of the tuning opening on the convexly extending outside of the measuring tube arc.

In the case of the example of an embodiment according to FIG. 4c, the centers of area of the tuning openings of the inner and outer couplers are shifted differently far from the coupler normal plane in the direction of the concavely extending inner side of the measuring tube arc, whereby the couplers are stiffer on the outside of the measuring tube arc. This leads, as a result, to a reduced maximum stress compared with couplers with symmetrically formed tuning opening. This reduced maximum stress occurs on the narrow side of the rim of the tuning opening of the inner coupler, and it amounts to $1.3 \times 10^{12}$, which is still, for instance, 70% of the maximum stress of the coupler of the CMD of FIG. 4b.

Figure 4D:
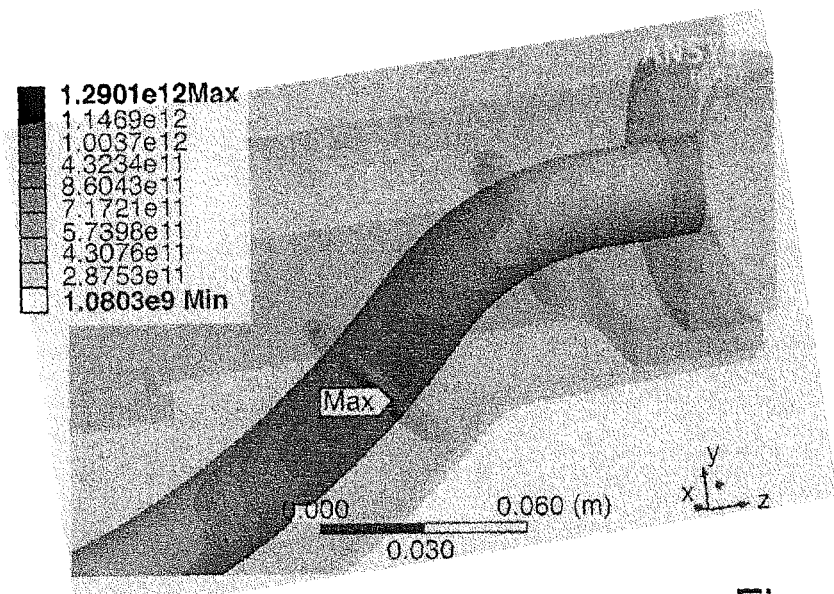
FIG. 4d: are simulation results for mechanical stress distributions in the measuring tubes of a CMD of the state of the art.
Figure 4E:
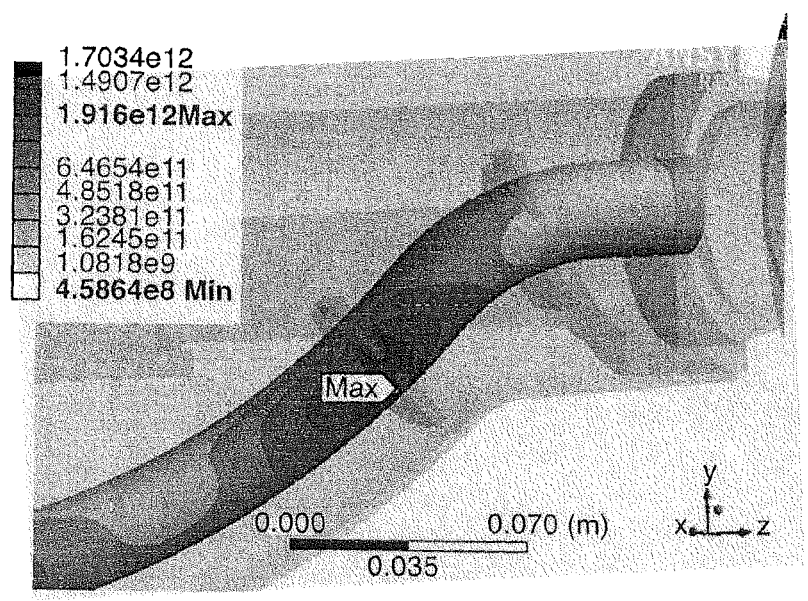
FIG. 4e: are simulation results for mechanical stress distributions in the measuring tubes of an example of an embodiment of a CMD of the invention.

FIGS. 4d and 4e show simulation results for the mechanical stress distributions in the measuring tubes of a CMD with, in each case, two inlet end and two outlet end couplers. As above, the numerical values are not to be considered as absolutes.

In the case of the CMD with solid couplers shown in FIG. 4d, the stress maximum of the measuring tubes occurs in or near the coupler normal plane of the inner coupler, in each case, on the side facing the other measuring tube and amounts in the case of a given oscillation amplitude of the measuring tubes, for example, to about $1.29 \times 10^{12}$.

In the case of the CMD shown in FIG. 4e, whose couplers have tuning openings, the stress maximum of the measuring tubes likewise occurs in or near the coupler normal plane of the inner coupler, in each case, on the side facing the other measuring tube and amounts in the case of equal oscillation amplitude to only $9.46 \times 10^{11}$ and is thus reduced by a good fourth. This is a considerable improvement.

The example of an embodiment of a CMD 100 of the invention shown in FIGS. 5a, 5b and 5c has two parallel, bent measuring tubes 110a, 110b, which extend between an inlet end collector 120a and an outlet end collector 120b, and are fixedly connected with such, for example, through roll expansion, hard soldering or welding. Extending between the collectors 120a, 120b is a solid support tube 124, which is fixedly connected with both collectors, whereby the collectors 120a, 120b are rigidly coupled with one another. Support tube 124 includes upper side openings 125a, 125b, through which the measuring tubes 110a, 110b are led from the collectors out and back into the support tube 124. Measuring tubes 110a, 110b are connected at the inlet end and at the outlet end, in each case, with two couplers 132a, 134a, 132b, 134b, wherein the couplers have tuning openings 146 between the measuring tubes. The couplers 132a, 132b, 134a, 134b define oscillation nodes for the measuring tubes. Between the inner couplers 132a, 132b, the measuring tubes 110a, 110b can freely oscillate, so that the position of the inner couplers essentially co-determine the oscillation characteristics of the oscillator formed by the measuring tubes 110a, 110b, especially the eigenfrequencies of oscillation modes of the oscillator.

For exciting oscillations, an exciter arrangement 140 is provided between the measuring tubes in the middle of the CMD 100 with reference to the longitudinal direction, or Z-axis, for example, an inductive exciter mechanism, which includes, for example, a plunger coil on one measuring tube and a plunger armature on the oppositely lying measuring tube. For registering oscillations of the measuring tubes, a first sensor arrangement 142a and a second sensor arrangement 142b are provided symmetrically to the exciter mechanism 140 in the longitudinal direction, which, in each case, is embodied as a inductive arrangement with a plunger coil on one tube and plunger armature on the other tube. Details are known to those skilled in the art, and need not be explained in further detail here. (In the interest of perspicuity, the positions of the exciter mechanism and the sensor arrangements are only shown in FIG. 5c, and omitted in FIGS. 5a and 5b).

The collectors 120a, 120b have terminal flanges 122a, 122b, by means of which the CMD can be installed in a pipeline. A mass flow is led through central openings 123b in the flanges through the CMD 100, especially its measuring tubes 110a, 110b, in order to measure the mass flow.

The measuring tubes 110a, 110b are connected at the inlet end and at the outlet end, in each case, with two couplers 132a, 134a, 132b, 134b, wherein the couplers have tuning openings 146 between the measuring tubes.

The invention claimed is:

1. At least one of a coriolis mass flow measuring device or density measuring device, comprising:
   at least two bent measuring tubes; said measuring tubes have measuring tube axes, which extend mirror symmetrically to a first mirror plane, which extends between said measuring tubes;
   at least one actuator arrangement;
   at least one sensor arrangement;
   a collector situated at the inlet end and at the outlet end, said measuring tubes are joined inlet end and outlet end with said collectors, wherein the inlet end and outlet end collectors are embodied stably in such a manner that each fulfills the functionality of a node plate;
   a support body, which connects the inlet end collector and the outlet end collector rigidly with one another; and
   at least one, plate-shaped couplers situated at the inlet end and the outlet end of each measuring tube, wherein:
   said measuring tubes are connected by means of said couplers pairwise with one another, in order to form an oscillator, said couplers have, in each case, two tube openings for said measuring tubes connected by said couplers, through which openings said measuring tubes are led, said measuring tubes are connected along their peripheries at least sectionally with said couplers;
   said at least one actuator arrangement is adapted to excite a bending oscillation wanted mode between said two measuring tubes of the oscillator,
   said sensor arrangement is adapted to register oscillations of said oscillator; and
   at each inlet end and outlet end, at least one coupler has, between said measuring tubes connected by the couplers, a tuning opening surrounded by a closed edge for influencing the oscillation characteristics of the oscillator.

2. The at least one of a coriolis mass flow measuring device or density measuring device as claimed in claim 1, wherein:
   said tuning openings have in the first mirror plane an extension of at least 30% of the diameter of said measuring tubes.

3. The at least one of a coriolis mass flow measuring device or density measuring device as claimed in claim 1, wherein:
   said tuning openings have in the first mirror plane a length, whose square amounts to not less than twice the area of the tuning opening.

4. The at least one of a coriolis mass flow measuring device or density measuring device as claimed in claim 1, wherein:
   the separation of said measuring tube axes at the position of said tuning openings amounts to no more than 1.5 times the outer diameter of the measuring tubes.

5. The at least one of a coriolis mass flow measuring device or density measuring device as claimed in claim 1, wherein:
   at least one coupler has in its coupler plane a convex envelope, whose area amounts to no more than five times the outer area of a measuring tube cross-section.

6. The at least one of a coriolis mass flow measuring device or density measuring device as claimed in claim 1, wherein:
   at the inlet end and at the outlet end, in each case, at least two couplers of a measuring tube pair connected by the couplers have such a tuning opening.

7. The at least one of a coriolis mass flow measuring device or density measuring device as claimed in claim 1, wherein:
   at the inlet end and at the outlet end, in each case, at least the two inner couplers of a measuring tube pair connected by the couplers have such a tuning opening; and
   the two inner couplers are the couplers farthest from the respective collector.

8. The at least one of a coriolis mass flow measuring device or density measuring device as claimed in claim 1, wherein:
   said at least one tuning opening is essentially symmetric to the first mirror plane.

9. The at least one of a coriolis mass flow measuring device or density measuring device as claimed in claim 1, wherein:
   at the inlet end and at the outlet end, in each case, the tuning opening of at least one coupler is asymmetric with reference to a coupler normal plane;
   said coupler normal plane extends parallel to the greatest principal axis of inertia of said coupler, perpendicular to said first mirror plane, and contacts a connecting line of said measuring tube axes extending perpendicular to said first mirror plane within the tuning opening.

10. The at least one of a coriolis mass flow measuring device or density density measuring device as claimed in claim 9, wherein:
    the separation of the outermost extension of said at least one tuning opening in said first mirror plane from said coupler normal plane on a first side of said coupler normal plane is less than on a second side of said coupler normal plane.

11. The at least one of a coriolis mass flow measuring device or density measuring device as claimed in claim 1, wherein:
    the separation between the outermost extension of said tuning opening in said first mirror plane and an outermost extension of said coupler in said first mirror plane on a first side of said coupler normal plane is less than on a second side of said coupler normal plane; and
    said coupler normal plane extends parallel to the greatest principal axis of inertia of said coupler, extends perpendicular to said first mirror plane, and contacts a connecting line of said measuring tube axes extending perpendicular to said first mirror plane within said tuning opening.

12. The at least one of a coriolis mass flow measuring device or density measuring device as claimed in claim 1, wherein:
    at the inlet end and at the outlet end, in each case, at least one coupler has a center of mass, which is removed from the coupler normal plane by a separation;
    said separation amounts to not less than 4% of the separation of said measuring tube axes in said coupler normal plane; and
    said coupler normal plane extends parallel to the greatest principal axis of inertia of the coupler, perpendicular to said first mirror plane, and contacts a connecting line of said measuring tube axes extending perpendicular to said first mirror plane within said tuning opening.

13. The at least one of a coriolis mass flow measuring device or density measuring device as claimed in claim 1, wherein:
    at the inlet end and at the outlet end, in each case, at least one coupler has a center of area of a minimum convex envelope, which center of area is removed from a coupler normal plane by a separation;

said separation amounts to not less than 4% of the separation of the measuring tube axes in the coupler normal plane;

said coupler normal plane extends parallel to the greatest principal axis of inertia of the coupler, perpendicular to said first mirror plane, and contacts a connecting line of said measuring tube axes extending perpendicular to said first mirror plane within said tuning opening.

14. The at least one of a coriolis mass flow measuring device or density measuring device in claim 1, wherein:

at the inlet end and at the outlet end, in each case, a first coupler and a second coupler have coupler specific coupler normal planes, each of which extends parallel to the greatest principal axis of inertia of its coupler, perpendicular to said first mirror plane, and contacts a connecting line of said measuring tube axes extending perpendicular to the first mirror plane within the tuning opening of the respective coupler;

said first coupler has a first center of mass, which is spaced from its coupler specific coupler normal plane by a first separation;

said second coupler has a first center of mass, which is spaced from its coupler specific coupler normal plane by a second separation; and the first separation differs from the second separation, wherein the difference amounts to not less than 5% of the smaller of the two separations.

15. The at least one of a coriolis mass flow measuring device or density measuring device as claimed in claim 1, wherein:

at the inlet end and at the outlet end, in each case, a first coupler and a second coupler have coupler specific coupler normal planes, each of which extends parallel to the greatest principal axis of inertia of its coupler, perpendicular to said first mirror plane, and contacts a connecting line of said measuring tube axes extending perpendicular to said first mirror plane within the tuning opening of its coupler;

at the inlet end and at the outlet end, in each case, a first coupler has a first center of area of a minimum convex envelope curve and a second coupler has a second center of area of a minimum convex envelope curve;

said first center of area is spaced from its coupler specific coupler normal plane by a first separation;

said second center of area is spaced from its coupler specific coupler normal plane by a second separation;

said first separation differs from said second separation;

the difference amounts not less than 5% of the smaller of the two separations.

16. The at least one of a coriolis mass flow measuring device or density measuring device as claimed in claim 1, wherein:

at the inlet end and at the outlet end, in each case, a first coupler and a second coupler have coupler specific coupler normal planes, each of which extends parallel to the greatest principal axis of inertia of its coupler, each of which extends perpendicular to said first mirror plane, and each of which contacts a connecting line of said measuring tube axes extending perpendicular to said first mirror plane within said tuning opening of its coupler;

said first coupler has a first tuning opening;
said second coupler has a second tuning opening; and
said first tuning opening differs from said second tuning opening in at least one of the following parameters: area of the tuning opening, length of the tuning opening, separation of the center of area of the tuning opening from its coupler normal plane.

17. The at least one of a coriolis mass flow measuring device or density measuring device as claimed in claim 1, wherein:

at the inlet end and at the outlet end, in each case, at least one tuning opening is bounded by edge sections, which in a section between said measuring tubes are formed on both sides by said measuring tubes.

18. The at least one of a coriolis mass flow measuring device or density measuring device as claimed in claim 17, wherein:

said edge sections formed by said measuring tubes have perpendicular to the greatest principal axis of inertia of the respective coupler, in each case, a length, which amounts to not less than 10% of the radius of the measuring tube, which forms the particular edge section of the tuning opening.

19. The at least one of a coriolis mass flow measuring device or density measuring device as claimed in claim 1, wherein:

said plate-shaped couplers have a material thickness, which amounts to no more than four times the wall thickness of said measuring tubes.

20. The at least one of a coriolis mass flow measuring device or density measuring device as claimed in claim 1, wherein:

said tuning openings have in the first mirror plane an extension of at least 50% of the diameter of said measuring tubes.

21. The at least one of a coriolis mass flow measuring device or density measuring device as claimed in claim 1, wherein:

said tuning openings have in the first mirror plane an extension of at least 50% of the diameter of said measuring tubes.

22. The at least one of a coriolis mass flow measuring device or density measuring device as claimed in claim 1, wherein:

said tuning openings have in the first mirror plane an extension of at least 70% of the diameter of said measuring tubes.

23. The at least one of a coriolis mass flow measuring device or density measuring device as claimed in claim 1, wherein:

said tuning openings have in the first mirror plane a length, whose square amounts to not less than four times the area of the tuning opening.

24. The at least one of a coriolis mass flow measuring device or density measuring device as claimed in claim 1, wherein:

said tuning openings have in the first mirror plane a length, whose square amounts to not less than eight times the area of the tuning opening.

25. The at least one of a coriolis mass flow measuring device or density measuring device as claimed in claim 1, wherein:

the separation of the measuring tube axes at the position of said tuning openings amounts to no more than 1.3 times the outer diameter of the measuring tubes.

26. The at least one of a coriolis mass flow measuring device or density measuring device as claimed in claim 1, wherein:

the separation of the measuring tube axes at the position of said tuning openings amounts to no more than 1.2 times the outer diameter of the measuring tubes.

27. The at least one of a coriolis mass flow measuring device or density measuring device as claimed in claim 1, wherein:
at least one coupler has in its coupler plane a convex envelope, whose area amounts to no more than 4½ times the outer area of a measuring tube cross-section.

28. The at least one of a coriolis mass flow measuring device or density measuring device as claimed in claim 1, wherein:
at least one coupler has in its coupler plane a convex envelope, whose area amounts to no more than 4 times the outer area of a measuring tube cross-section.

29. The at least one of a coriolis mass flow measuring device or density measuring device as claimed in claim 1, wherein:
at the inlet end and at the outlet end, in each case, at least one coupler has a center of mass, which is removed from the coupler normal plane by a separation, wherein the separation amounts to not less than 8% of the separation of the measuring tube axes in the coupler normal plane, wherein the coupler normal plane extends parallel to the greatest principal axis of inertia of the coupler, perpendicular to the first mirror plane, and contacts a connecting line of the measuring tube axes extending perpendicular to the first mirror plane within the tuning opening.

30. The at least one of a coriolis mass flow measuring device or density measuring device as claimed in claim 1, wherein:
at the inlet end and at the outlet end, in each case, at least one coupler has a center of area of a minimum convex envelope, which center of area is removed from a coupler normal plane by a separation;
said separation amounts to not less than 8% of the separation of the measuring tube axes in the coupler normal plane:
said coupler normal plane extends parallel to the greatest principal axis of inertia of the coupler, perpendicular to said first mirror plane, and contacts a connecting line of said measuring tube axes extending perpendicular to said first mirror plane within said tuning opening.

31. The at least one of a coriolis mass flow measuring device or density measuring device as claimed in claim 14, wherein:
the first separation differs from the second separation, wherein the difference amounts to not less than 10% of the smaller of the two separations.

32. The at least one of a coriolis mass flow measuring device or density measuring device as claimed in claim 15, wherein:
said first separation differs from the second separation, wherein the difference amounts to not less than 10% of the smaller of the two separations.

33. The at least one of a coriolis mass flow measuring device or density measuring device as claimed in claim 17, wherein:
said edge sections formed by said measuring tubes have perpendicular to the greatest principal axis of inertia of the respective coupler, in each case, a length, which amounts to not less than 20% of the radius of the measuring tube, which forms the particular edge section of the tuning opening.

34. The at least one of a coriolis mass flow measuring device or density measuring device as claimed in claim 17, wherein:
said edge sections formed by said measuring tubes have perpendicular to the greatest principal axis of inertia of the respective coupler, in each case, a length, which amounts to not less than 30% of the radius of the measuring tube, which forms the particular edge section of the tuning opening.

35. The at least one of a coriolis mass flow measuring device or density measuring device as claimed in claim 1, wherein:
said plate-shaped couplers have a material thickness, which amounts to no more than three times, the wall thickness of the measuring tubes.

\* \* \* \* \*